United States Patent [19]

Elliott et al.

[11] Patent Number: 4,875,922
[45] Date of Patent: Oct. 24, 1989

[54] PYRIMIDINE DERIVATIVES

[75] Inventors: Raymond Elliott, Lower Earley, nr. Reading; David A. Griffin, Wokingham; Raymond S. Gairns, Whitefield, all of England

[73] Assignee: Imperial Chemical Industries PLC, London, England

[21] Appl. No.: 133,450

[22] Filed: Dec. 15, 1987

[30] Foreign Application Priority Data

Dec. 23, 1986 [GB] United Kingdom ................. 8630824
Jul. 3, 1987 [GB] United Kingdom ................. 8715684

[51] Int. Cl.⁴ .................. A01N 43/54; A61K 31/505; C07D 239/26
[52] U.S. Cl. ........................................ 71/76; 514/256; 544/335
[58] Field of Search ........................ 544/335; 514/256; 71/76

[56] References Cited

U.S. PATENT DOCUMENTS 3,818,009 6/1974 Taylor et al. ...................... 544/335
3,868,244 2/1975 Taylor et al. ............................ 71/76
3,887,708 6/1975 Taylor et al. ............................ 71/90

Primary Examiner—Richard L. Raymond
Assistant Examiner—James H. Turnipseed
Attorney, Agent, or Firm—Cushman, Darby & Cushman

[57] ABSTRACT

A pyrimidine derivative having the general formula (I):

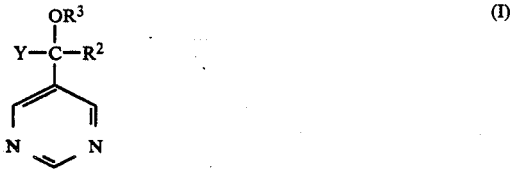

and stereoisomers thereof, wherein Y is optional substituted cyclopropyl or optionally substituted 1-methylcyclopropyl or is the group:

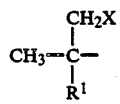

wherein $R^1$ is hydrogen or methyl; X is hydrogen or halogen; $R^2$ is an optionally substituted alkyl, cycloalkyl, cycloalkylalkyl or alkylcycloalkyl group, each of said groups containing a total of from 4 to 8 carbon atoms; or is an optionally substituted alkenyl, cycloalkenyl, cycloalkenylalkyl, or alkylcycloalkenyl group, each of said groups containing a total of from 4 to 8 carbon atoms; or is an optionally substituted alkynyl group containing a total of from 4 to 8 carbon atoms; and $R^3$ is hydrogen, an alkyl group containing from 1 to 4 carbon atoms, an alkenyl group containing from 3 to 4 carbon atoms or an alkynyl group containing from 3 to 4 carbon atoms; and agrochemically acceptable salts, esters and metal complexes of the compounds of formula (I) wherein $R^3$ is hydrogen. These compounds are useful as plant growth regulating agents and fungicides.

11 Claims, No Drawings

PYRIMIDINE DERIVATIVES

This invention relates to pyrimidine derivatives useful as plant growth regulating agents and fungicides, to processes for preparing them, to compositions containing them and to methods of regulating plant growth using them.

In British patent specification No. 1,218,623 there are disclosed certain substituted 5-pyrimidine compounds having fungicidal activity.

According to the present invention there is provided a pyrimidine derivative having the general formula (I)

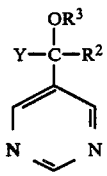 (I)

and stereoisomers thereof, wherein Y is optionally substituted cyclopropyl or optionally substituted 1-methylcyclopropyl or is the group:

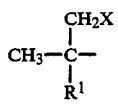

wherein $R^1$ is hydrogen or methyl; X is hydrogen or halogen; $R^2$ is an optionally substituted alkyl, cycloalkyl, cycloalkylalkyl or alkylcycloalkyl group, each of said groups containing a total of from 4 to 8 carbon atoms; or is an optionally substituted alkenyl, cycloalkenyl, cycloalkenylalkyl, or alkylcycloalkenyl group, each of said groups containing a total of from 4 to 8 carbon atoms; or is an optionally substituted alkynyl group containing a total of from 4 to 8 carbon atoms; and $R^3$ is hydrogen, an alkyl group containing from 1 to 4 carbon atoms, an alkenyl group containing from 3 to 4 carbon atoms or an alkynyl group containing from 3 to 4 carbon atoms; and agrochemically acceptable salts, esters and metal complexes of the compounds of formula (I) wherein $R^3$ is hydrogen.

The compounds of the invention may contain one or more chiral centres. Such compounds are generally obtained in the form of racemic mixtures. However, these and other mixtures can be separated into the individual isomers by methods known in the art, and this invention embraces such isomers.

Where X is halogen, it is preferably chlorine or fluorine.

Optional substituents which may be present in the group Y include lower alkyl (for example $C_1$ to $C_4$ alkyl) and halogen, especially monohalogen, for example chlorine or fluorine.

Optional substituents which may be present in the group $R^2$ include halogen, especially monohalogen, for example chlorine or fluorine.

When $R^2$ is an optionally substituted cycloalkylalkyl or cycloalkenylalkyl group (that is a group in which the cycloalkyl or cycloalkenyl moiety is linked to the rest of the molecule through an alkyl chain), the optionally substituted cycloalkyl or cycloalkenyl group preferably contains from 3 to 6, for example from 3 to 5 ring carbon atoms. Optional substitutents which may be present in the cycloalkyl or cycloalkenyl ring include halogen and lower alkyl (for example $C_1$ to $C_4$ alkyl).

When $R^2$ is an alkenyl group, it is preferably a group:

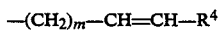

where $R^4$ is an optionally substituted alkyl group containing from (2-m) to (6-m) carbon atoms, or an optionally substituted cycloalkyl or cycloalkylalkyl group containing from 3 to (6-m) carbon atoms and m is an integer from 0 to 2, especially 0 or 1. Especially preferred alkenyl groups $R^2$ have the formula:

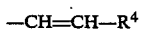

wherein $R^4$ is an optionally substituted alkyl group containing from 2 to 6 carbon atoms.

When $R^2$ is an alkynyl group it is preferably a group:

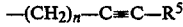

wherein $R^5$ is an optionally substituted alkyl group containing from (2-n) to (6-n) carbon atoms, or an optionally substituted cycloalkyl or cycloalkylalkyl group containing from 3 to (6-n) carbon atoms and n is an integer from 0 to 2, especially 0 or 1. Especially preferred alkynyl groups $R^2$ have the formula:

wherein $R^5$ is an optionally substituted alkyl group containing from 2 to 6 carbon atoms, and especially from 3 to 4 carbon atoms.

Preferred groups $R^3$ are hydrogen, methyl, ethyl, allyl or propargyl. Hydrogen is especially preferred.

The present invention includes agrochemically acceptable salts, esters and metal complexes of the compounds of formula (I) wherein $R^3$ is hydrogen. As examples of esters there may be mentioned for example acetates or benzoates. As examples of salts there may be mentioned for example toluene sulphonate salts, dodecylbenzene sulphonate salts, hydrochloride salts, hydrobromide salts and orthophosphate salts. Without limitation of the generality of the above statement, the present invention also includes any compound which breaks down in agrochemical use to a compound of formula (I).

Examples of the compounds of the invention are presented in Table 1 in which the values for $R^1$, $R^2$ and $R^3$ in the general formula (I) above are as indicated.

TABLE I

| COMPOUND NO | $R^1$ | $R^2$ | $R^3$ | X | MELTING POINT (°C.) | COMMENTS |
|---|---|---|---|---|---|---|
| 1 | H | $-C{\equiv}C-CH_2-CH_2-CH_2-CH_3$ | H | H | Oil | |
| 2 | H | $-C{\equiv}C-CH_2-CH_2-CH_3$ | H | H | Oil | |
| 3 | H | $-CH_2-CH_2-CH_2-CH_2-CH_3$ | H | H | Oil | |
| 4 | H | $-C{\equiv}C-CH_2-CH-(CH_3)_2$ | H | H | 54.5-55.5 | |
| 5 | H | $-C{\equiv}CH-(CH_3)-CH_2-CH_3$ | H | H | Oil | |
| 6 | H | $-CH_2-CH_2-CH(CH_3)-CH_2-CH_3$ | H | H | Oil | |
| 7 | H | $-CH_2-CH_2-CH_2-CH(CH_3)_2$ | H | H | Oil | |

TABLE I-continued

| COMPOUND NO | R¹ | R² | R³ | X | MELTING POINT (°C.) | COMMENTS |
|---|---|---|---|---|---|---|
| 8 | H | —C≡C—CH₂—CH₂—CH₂Cl | H | H | Oil | |
| 9 | H | —C≡C—CH(CH₃)₂ | H | H | 79–79.5 | |
| 10 | H | —C≡C—C(CH₃)₃ | H | H | 91–92 | |
| 11 | H | —C≡C—CH₂—CH(CH₃)—CH₂—CH₃ | H | H | gum | |
| 12 | H | —C≡C—CH₂—CH₂—CH(CH₃)₂ | H | H | 54–55 | |
| 13 | H | —CH₂—CH₂(CH₃)₂ | H | H | gum | |
| 14 | CH₃ | —C≡C—CH₂—CH₂—CH₃ | H | H | 64–66 | |
| 15 | CH₃ | —CH₂—CH₂—CH₂—CH₂—CH₃ | H | H | 66–67 | |
| 16 | CH₃ | —C≡C—CH₂—CH—(CH₃)₂ | H | H | 65–67 | |
| 17 | CH₃ | —CH₂—CH₂—CH₂—CH(CH₃)₂ | H | H | gum | |
| 18 | CH₃ | —C≡C—CH(CH₃)₂ | H | H | 84–85 | |
| 19 | CH₃ | —C≡C—CH₂—CH₂—CH₂—Cl | H | H | 93–94 | |
| 20 | H | —CH₂—CH₂—C(CH₃)₃ | H | H | 87–87.5 | |
| 21 | H | —CH₂—CH₂—CH₂—CH(CH₃)—CH₂—CH₃ | H | H | gum | |
| 22 | H | CH₂—CH₂—CH₂—CH₂—CH(CH₃)₂ | H | H | gum | |
| 23 | H | —C≡C—CH₂—CH₂—CH₂—CH₂—CH₃ | H | H | oil | |
| 24 | H | —C≡C—CH₂—CH₂—CH₂—CH₂—CH₂—CH₃ | H | H | oil | |
| 25 | H | —CH≡CH—CH₂—CH₂—CH₂ | H | H | gum | cis isomer |
| 26 | H | —CH₂—CH₂—CH₂—CH₂—CH₂—CH₂—CH₃ | H | H | gum | |
| 27 | H | —CH₂—(cyclopentyl) | H | H | 82.2–85.2 | |
| 28 | H | —CH₂—(cyclopentenyl) | H | H | gum | |
| 29 | CH₃ | —CH₂—CH₂—CH(CH₃)₂ | H | H | 89–91 | |
| 30 | CH₃ | —CH₂—CH₂—CH₂—CH₂—CH₂—CH₃ | H | H | 91–91.5 | |
| 31 | CH₃ | —C≡C—CH₂—CH₂—CH₂—CH₃ | H | H | 75–77 | |
| 32 | CH₃ | —C≡C—CH₂—CH₂—CH₂—CH₂—CH₃ | H | H | 89–89.5 | |
| 33 | CH₃ | —C≡C—CH₂—CH₂—CH₂—CH₂—CH₂—CH₃ | H | H | 39–40 | |
| 34 | CH₃ | —CH₂—CH₂—CH₂—CH₂—CH₂—CH₃ | H | H | 55–56 | |
| 35 | CH₃ | —CH₂—CH₂—CH₂—CH₃ | H | H | | |
| 36 | CH₃ | —C≡C—CH₂—CH₂—Cl | H | H | 84.5–85 | |
| 37 | CH₃ | —C≡C—CH₂—CH₂—CH₂—CH₂—Cl | H | H | 97–100 | |
| 38 | CH₃ | —C≡C—CH₂—CHCl—CH₂—CH₃ | H | H | 108–114 | |
| 39 | CH₃ | —CH=CH—C(CH₃)₃ | H | H | 123–128 | trans isomer |
| 40 | CH₃ | —CH₂—(cyclopentenyl) | H | H | 79–81 | |
| 41 | CH₃ | —CH₂—CH₂—(cyclopropyl) | H | H | gum | |
| 42 | CH₃ | —CH₂—(cyclopentyl) | H | H | 97.7–100.7 | |
| 43 | CH₃ | —C≡C—CHCl—CH₂—CH₂—CH₃ | H | H | 107–110 | |
| 44 | CH₃ | —C≡C—CHCl—CH₂—CH₃ | H | H | 69–72 | |
| 45 | CH₃ | —CH₂—C≡C—CH₃ | H | H | 117 | |
| 46 | CH₃ | —CH₂—C≡C—CH₂CH₃ | H | H | 47–48 | |
| 47 | CH₃ | —CH₂—CH₂—CH₂—CH₂—CH₂Cl | H | H | 65–70 | |
| 48 | CH₃ | —CH₂—CH₂—CH₂—CH₂—CH₂—CH₂Cl | H | H | 76–79 | |
| 49 | CH₃ | —CH=CH—C(CH₃)₃ | H | F | 126–128 | trans isomer |
| 50 | H | —C≡C—CH₂—CH(CH₃)—CH₃ | —CH₂—C≡CH | H | oil | |
| 51 | H | —C≡C—CH₂—CH(CH₃)—CH₃ | CH₃ | H | oil | |
| 52 | H | —C≡C—CH₂—CH(CH₃)—CH₃ | C₂H₅ | H | oil | |
| 53 | H | —C≡C—CH₂—CH(CH₃)—CH₃ | —CH₂—CH=CH₂ | H | oil | |
| 54 | H | —C≡C—CH₂—CH(CH₃)—CH₃ | H | H | oil | acetate ester |
| 59 | H | —CH₂—CH₂—CH₂—CH₃ | H | H | gum | |
| 60 | H | —C≡C—(cyclopentyl) | H | H | 65–67 | |
| 61 | CH₃ | —CH=CH—CH₂—CH(CH₃)₂ | H | H | gum | |

TABLE I-continued

| COMPOUND NO | R¹ | R² | R³ | X | MELTING POINT (°C.) | COMMENTS |
|---|---|---|---|---|---|---|
| 63 | H | —CH≡CH—CH₂—CH(CH₃)₂ | H | H | gum | |

TABLE I (a)

| COMPOUND NO | Y | R² | MELTING POINT (°C.) | COMMENTS |
|---|---|---|---|---|
| 55 | cyclopropyl-CH₃ | —CH=CH—C(CH₃)₃ | 109–110 | trans isomer |
| 56 | cyclopropyl | —C≡C—CH₂—CH(CH₃)₂ | gum | |
| 57 | cyclopropyl | —C≡C—CH₂—CH₂—CH₃ | gum | |
| 58 | cyclopropyl | —CH₂—CH₂—CH₂—CH₂—CH₃ | gum | |
| 62 | cyclopropyl-CH₃ | —CH₂—CH₂—C(CH₃)₃ | 107–108 | |

Compounds of general formula (I) above wherein $R^3$ is hydrogen and Y is as defined may be prepared by reacting a compound of general formula (II):

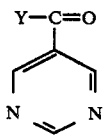

(II)

with an organometallic compound which may be represented by the general formula (III):

$$R^2M \quad (III)$$

where M is a suitable metal, for example lithium, magnesium, titanium or zirconium.

The reaction conveniently takes place in a solvent such as diethylether, tetrahydrofuran or dichloromethane at $-80°$ C. to $+80°$ C. in an inert atmosphere. The product is obtained by quenching with a proton donor. When M is magnesium, the organometallic compound is more specifically $R^2$—Mg—halogen. When M is titanium, the organometallic compound is more specifically $R^2$—Ti(O—alkyl)$_3$. When M is zirconium, the organometallic compound is more specifically $R^2$—Zr—(-O—alkyl)$_3$.

When $R^2$ in formula (I) contains a halogen substituent, for example chlorine, it may be convenient to prepare the corresponding hydroxy product, which is then converted into the chloride by one of the standard literature methods e.g., treatment with mesyl chloride followed by treatment with lithium chloride. If desired, the hydroxy product corresponding to $R^2M$ may be protected during reaction with the compound of general formula (II) by the formation of a suitable derivative such as a silyl ether derivative.

The compounds of general formula (I) wherein $R^3$ is hydrogen may also be prepared by reacting a ketone of general formula (IV), wherein $R^1$ and $R^2$ are as defined with an organometallic compound which may be represented by the general formula (V) wherein M is a suitable metal, for example lithium:

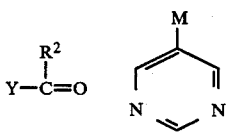

(IV)     (V)

The reaction preferably takes place in a suitable solvent such as deithyl ether or tetrahydrofuran at a temperature of from $-120°$ C. to $+80°$ C. and in an inert atmosphere. The product is obtained by quenching with a suitable proton donor.

The ketones of general formula (II) and (IV) are known compounds which may be prepared using standard methods set out in the literature.

Olefinic alcohols wherein $R^2$ is the group —CH=CH—$R^5$ wherein $R^5$ is as defined above may be made by the reduction of the corresponding acetylenic alcohol wherein $R^2$ is —C≡C—$R^5$. Suitable reducing agents include hydrogen in the presence of a suitable catalyst such as palladium on a support such as carbon (for example a Lindlar catalyst); or a metal hydride reducing agent such as lithium aluminium hydride, "Red-Al" (sodium bis [2-methoxyethoxy] aluminium hydride) or sodium borohydride/palladium (II) chloride in a suitable solvent such as ether or tetrahydrofuran.

Similarly, compounds of formula (I) wherein $R^2$ is a group:

$$-CH_2CH_2-R^5$$

where $R^5$ is as defined above atoms, may be made by the complete reduction of the corresponding acetylenic alcohol, $-C\equiv C-R^5$. Suitable reducing agents include hydrogen in the presence of a suitable reducing agent as palladium' rhodium or platinum on a support such as carbon and in a suitable solvent such as methanol, ethanol or acetic acid.

The ethers (wherein $R^3$ is alkyl) and esters of the invention may be made from the corresponding hydroxy compound by reaction with the appropriate halide, acid chloride or acid anhydride in the presence of a suitable base.

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in, cereals such as wheat, barley and rice and in oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. They may also have an effect on flower head emergence in, for example, grasses. The compounds can also stunt weed species present in the grasses; examples of such weed species are sedges (e.g., Cyperus spp.) and dicotyledonous weeds (e.g., daisy, plantain, knotweed, speedwell, thistle, docks and ragwort). The growth of non-crop vegetation (e.g., weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth of undesirable species.

The dwarfing may also be useful in miniaturising ornamental, household, garden and nursery plants (e.g., poinsettias, chrysanthemums, carnations, tulips and daffodils).

As indicated above, the compounds can also be used to stunt woody species. This property can be used to control hedgerows or to shape or reduce the need for pruning, of fruit trees (eg, apples, pears, cherries, peaches, vines etc).

The plant growth regulating effect may (as implied above) manifest itself in an increase in crop yield; or in an ability in orchards and other crops to increase fruit set, pod set and grain set. Some coniferous trees are not significantly stunted by the compounds so the compounds could be useful in controlling undesirable vegetation in conifer nurseries.

In the potato, vine control in the field and inhibition of sprouting in the store may be possible.

In addition the compounds may be useful as abscision agents resulting in thinning of fruit on the tree and an increase in fruit quality.

Other plant growth regulating effects caused by the compounds include alteration of leaf angle and changes in leaf morphology (both of which may permit increased light interception and utilization) and control of tillering in monocotyledonous plants. Improved light interception is of value in all major world crops, e.g., wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (e.g., rice), the number of flowering shoots per unit area may be increased thereby increasing the overall grain yield of such crops. In the alternative, reduced tillering may on occasion increase the productivity of those remaining tillers to the extent the overall increase in yield is obtained. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, e.g., as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, e.g., improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (e.g., turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (i.e. the harvested yield as a proportion of the total dry matter produced) by altering dry matter partitioning. This applies to all the aforementioned root, pod, cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants. When applied as seed treatments at low rates the compounds can have a growth stimulating effect on plants.

It is to be understood that not all the compounds of the present invention will necessarily show all the above mentioned plant growth regulating effects. Thus whilst there may be advantages in compounds which have a broad spectrum of plant growth regulating effects against a wide range of species, compounds having a high specific activity with respect to a particular species and/or plant growth regulating effect may also be of great benefit.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.01 to 15, preferably 0.1 to 5, kg per hectare is used. With the use of biodegradable polymeric slow release granules rates of 1 to 10g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may be used as such for plant growth regulating purposes but are more conveniently formulated into compositions for such usage. The invention thus provides a plant growth regulating composition comprising a compound of general formula (I) as hereinbefore defined, or a salt or metal complex thereof; and, optionally, a carrier or diluent.

The invention also provides a method of regulating plant growth, which comprises applying to the plant, to seed of a plant or to the locus of a plant or seed, a compound, or a salt or metal complex thereof, as hereinbefore defined, or a composition combining the same.

The compounds, salts, metal complexes, ethers and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules. Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g., 2-ethoxyethanol and 2-butoxyethanol).

The compositions to be used as sprays may also be in the form of aerosols wherein the formulation is held in a container under pressure in the presence of a propellant, e.g., fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a micro-encapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (e.g., nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g., wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (e.g., alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% to 10%, or 0.01% to 10%, by weight of active ingredient(s) may be used.

The compositions of this invention can comprise also one or more additional compound(s) having biological activity, e.g., compounds having similar or complementary fungicidal or plant growth activity or compounds having plant growth regulating, herbicidal or insecticidal activity.

The additional fungicidal compound can be, for example, one which is capable of combating ear diseases of cereals (e.g., wheat) such as *Septoria, Gibberella* and *Helminthosporium* spp., seed and soil borne diseases and downy and powdery mildews on grapes and powdery mildew and scab on apple etc. Examples of suitable additional fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetylaluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazatine, dodine fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenaponil, ofurace, propiconazole, etaconazole and fenpropemorph and fenpropidine.

The compounds of general formula (I) can be mixed with soil, peat or other rooting media for the protection of plants against seed-borne, soil-borne or foliar fungal diseases.

Suitable additional insecticides are Pririmor, Croneton, dimeth- oate, Metasystox, pyrethroid insecticides and formothion.

The other, additional, plant growth regulating compound can be one which controls weeds or seedhead formation, improves the level or longevity of the plant growth regulating activity of the compounds of general formula (I), selectively controls the growth of the less desirable plants (e.g., grasses) or causes the compound of general formula (I) to act faster or slower as a plant growth regulating agent. Some of these other agents will also be herbicides.

Examples of suitable plant growth regulating compounds, which can display synergy in admixture, or use, with the invention compounds are the gibberellins (e.g., $GA_3$, $GA_4$ or $GA_7$), the auxins (e.g., indoleacetic acid, indolebutyric acid, naphthoxyacetic acid or naphthylacetic acid), the cytokinins (e.g., kinetin, diphenylurea, benzimidazole, benzyladenine or benzylaminopurine), phenoxyacetic acids (e.g., 2,4-D or MCPA), substituted benzoic acids (e.g., triiodobenzoic acid), morphactins (e.g., chlorfluorecol), maleic hydrazide, glyphosate, glyphosine, long chain fatty alcohols and acids, dikegulac, fluoridamid, mefluidide, substituted quaternary ammonium and phosphonium compounds (e.g., chlormequat* chlorphonium or mepiquat chloride*), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydroxybenzonitriles (e.g., bromoxynil), difenzoquat*, benzoylprop-ethyl 3,6-dichloropicolinic acid, fenpentezol, triapenthanol, flurpirimidol, paclobutrazol, tetcyclacis and tecnazene. Synergy will be most likely to occur with those of the foregoing which are quaternary ammonium compounds and with those marked with an asterisk.

For certain applications, for example in the injection of the compounds of the invention into trees or plants, it is desirable that the compounds have a relatively high solubility in water, for example a solubility in excess of 10 parts per million. The compounds may alternatively be injected into the tree in the form of an organic solution, for example a solution in a lower alcohol.

For certain applications it is also desirable that the compound has a low persistancy in soil to prevent carry-over to adjacent crops or even crops planted subsequently in the same soil. Preferably the compound for use in such applications has a half life in the soil of less than 20 weeks.

The invention is illustrated by the following examples, in which Infra red characterisation of the compounds is given as $\gamma$ maximum (cm$^{-1}$); NMR characterisation of the compounds is given in terms of $\delta_H$; and mass sprectroscopy analysis is given in terms of m/z.

EXAMPLE 1

This Example illustrates the preparation of 2-methyl-1-(hex-1-yne)-1-(pyrimidin-5-yl)-propan-1-ol (Compound No. 1 of Table 1).

To a solution of n-butyl lithium (10 ml of 2.6 M, 26 mmol) in dry tetrahydrofuran (40 ml) at $-78°$ C. was added a solution of 5-bromopyrimidine (3.18 g, 20 mmol) in dry tetrahydrofuran (20 ml) over a period of 5 minutes. This was followed immediately by the addition of a solution of 2-methylnon-4-yne-3-one (3.0 g, 20 mmol) in dry tetrahydrofuran (40 ml). The reaction mixture was allowed to warm to room temperature, stirred for 3 hours, and then poured into 10% ammonium chloride solution. The aqueous solution was extracted with ether (2×250 ml). The organics extract was collected, washed with water and brine, dried over magnesium sulphate and the solvent removed. Flash chromatography (silica gel, petrol/ether elution) of the residue gave the product as a yellow oil (1.5 g, 32.3%), boiling point 250° C. under 0.3 mm of mercury pressure.

Analysis Found: C, 72.4; H, 8.1; N, 12.0 $C_{14}H_{20}N_2O$ requires: C, 72.4; H, 8.6; N, 12.1%);

Infra red 3250, 2220, 1560, 1400, 1160, 1100, 740 cm$^{-1}$;

NMR (90 MHz; CDCl$_3$) 0.86 (3H,d, J=6.5 Hz), 0.94 (3H,t, J=6.5 hz), 1.04 (3H,d, J=6.5 Hz), 1.18-1.74 (4H,m), 2.07 (1H,m), 2.32 (2H,t, J=6.5 Hz), 2.72 (1H,s), 8.94 (2H,s), 9.15 (1H,s);

m/z 232 (M+), 189 (100%), 147, 133, 107, 79, 43.

EXAMPLE 2

This Example illustrates the preparation of 2-methyl-1-(pent-1-yne)-1-(pyrimidin-5-yl)-propan-1-ol (Compound No. 2 of Table 1).

To a solution of n-butyl lithium (10 ml of 2.6 M, 26 mmol) in dry tetrahydrofuran (20 ml) at $-78°$ C., was added a solution of 5-bromopyrimidine (3.18 g, 20 mmol) in dry tetrahydrofuran (15 ml) over a period of 5 minutes. This was followed immediately by the addition of a solution of 2-methyloct-4-yne-3-one (2.76 g, 20 mmol) in dry tetrahydrofuran (15 ml). The reaction mixture was allowed to warm to room temperature, stirred for 4 hours, and then poured into 10% ammonium chloride solution. The aqueous solution was extracted with ether (2×250 ml), the organics were collected, washed with water and brine, dried over magnesium sulphate and the solvent removed. Flash chromatography (silica gel, petrol/ether elution) of the residue gave the product as a yellow oil 93.22 g, 73.86%).

Analysis Found: C, 71.9; H, 8.5; N, 13.0 $C_{13}H_{18}N_2O$ requires: C, 71.6; H, 8.3; N, 12.8%;

Infra red 3260, 2960, 2210, 1560, 1400, 1220, 1160, 1120, 1030, 890, 730 cm$^{-1}$;

NMR (90 MHz; CDCl$_3$) 0.84 (3H,d, J=6.5 Hz), 1.0 (3H,t, J=6.5 Hz), 1.05 (3H,d, J=6.5 Hz), 1.6 (2H, sx, J=6.5 Hz), 2.07 (1H, spt, J=6.5 Hz), 2.28 (2H, t, J=6.5 Hz), 2.68 (1H,s), 8.92 (2H,s), 9.13 (1H,s);

m/z 218 (M+), 175 (100%)

EXAMPLE 3

This Example illustrates the preparation of 2-methyl-1-pentyl-1-(pyrimidin-5-yl)-propan-1-ol (Compound No. 3 of Table 1).

To a solution of Compound No. 2 of Example 2 (1.0 g, 4.5 mmol) in ethanol (100 ml) was added palladium/-charcoal (1 g of 5%) and the reaction vessel was charged with hydrogen (60 psi) at 50° C. After 24h the vessel was discharged, the catalyst filtered off and the solvent removed. Flash chromatography (silica gel, petrol/ethyl elution) of the residue gave the product as a yellow oil (0.38 g, 38.77%).

Analysis Found: C, 70.6; H, 9.7; N, 12.5 $C_{13}H_{22}N_2O$ requires: C, 70.3; H, 9.9; N, 12.6%;

Infra red 3360, 2980, 1560, 1470, 1420, 1220, 1130, 910, 760 cm$^{-1}$;

NMR (90 MHz; CDCl$_3$) 0.80 (3H,d, J=6.5 Hz), 0.85 (3H,t, J=6.5 Hz), 0.98 (3H,d, J=6.5 Hz), 1.08—1.4 (6H,m), 1.88 (1H,s), 1.88 (2H,t, J=6.5 Hz), 2.05 (1H,m), 8.78 (2H,s), 9.14 (1H,s);

m/z 222 (M+), 179 (100%), 151.

EXAMPLE 4

This Example illustrates the preparation of 2-methyl-1-(4-methylpent-1-yne)-1-(pyrimidin-5-yl)-propan-1-ol (Compound No. 4 of Table 1).

Stage 1

Preparation of 2-methyl-1-(pyrimid-5-yl)-propan-1-ol.

To a solution of n-butyl lithium (20 ml of 2.6 M, 52 mmol) in dry tetrahydrofuran (60 ml) at $-78°$ C., was added a cold solution of 5-bromopyrimidine (6.36 g, 40 mmol) in dry tetrahydrofuran (30 ml) over a period of 5 minutes. After 10 minutes a cold solution of iso-butyraldehyde (2.88 g, 40 mmol) in dry tetrahydrofuran (30 ml) was added dropwise. The mixture was allowed to warm to room temperature and stirred for 16 hours. The reaction mixture was poured into water and extracted with ether (2×100 ml). The organic layer was collected, washed with brine and dried over magnesium sulphate before removing the solvent. Flash chromatography (silica gel, petrol/ether elution) gave the product as a yellow oil.

Stage 2

Preparation of 2-methyl-1-(pyrimid-5-yl)-propan-1-one.

To a suspension of chromium (VI) oxide (12.87 g, 65 mmol) in dry dichloromethane (500 ml) was added dry pyridine (10.27 g, 130 mmol) and the mixture stirred for 0.5 h. Then a solution of 2-methyl-1-(pyrimid-5-yl)-propan-1-ol, prepared in stage 1, (1.52 g, 10 mmol) in dry dichloromethane (100 ml) was added dropwise with stirring. After 2 hours the reaction mixture was poured into ether (1000 ml) and then filtered. The filtrate was washed with copper sulphate solution (4×400 ml), brine solution (2×400 ml), and dried over magnesium sulphate before removing the solvent. Flash chromatography (silica gel, petrol/ether elution) gave the product as a colourless oil (0.72 g, 48%).

Stage 3

To a solution of 4-methylpent-1-yne (0.27 g, 3.3 mmol) in dry tetrahydrofuran (30 ml) at $-78°$ C. was added n-butyl lithium (1.35 ml of 2.6 M, 3.5 mmol) and the mixture was stirred for 10 minutes. To this mixture was added chlorotitanium tris-isopropoxide (3.3 ml of 1M, 3.3 mmol). After 20 minutes a solution of 2-methyl-1-(pyrimid-5-yl)-propan-1-one from Stage 1 (0.5 g, 3.3 mmol) in dry tetrahydrofuran (20 ml) was added and the mixture allowed to warm to room temperature. After 16 hours the reaction mixture was poured into water and extracted with ether (2×100 ml). The combined organic extracts were washed with saturated brine, dried over magnesium sulphate, and the solvent removed. Flash chromatography (silica gel, petrol/ether elution) gave the product as a yellow oil (0.285 g, 37%).

A different sample prepared in the same way crystallised on standing to give a pale yellow solid (melting point 54.5°-55.5° C.).

Analysis Found: C, 71.9; H, 9.2; N, 12.0 $C_{14}H_{20}N_2O$ requires C, 72.4; H, 8.6; N, 12.1%;

Infra red 3300, 2980, 2220, 1560, 1470, 1430, 1410, 1280, 1230, 1170, 1030, 910, 890, 730 cm$^{-1}$;

NMR (90 MHz; CDCl$_3$) 0.87 (3H,d, J=7.2 Hz), 1.02 (6H,d, J=7.2 Hz), 1.06 (3H,d, J=7.2 Hz), 1.6 —2.2 (2H,m), 2.04 (2H,d, J=6.3 Hz), 2.2 (1H, br), 8.93 (2H,s), 9.13 (1H,s).

EXAMPLE 5

2-Methyl-1-(3-methylpent-1-yne)-1-(pyrimidin-5-yl)-propan-1-ol (Compound No. 5 of Table 1) was prepared using the general method of Example 4 by reacting 3-methylpent-1-yne with 2-methyl-1-pyrimid-5-yl-propan-1-one. The product was a colourless oil having a boiling point of 210° C. under 0.75 mmHg and characterised as follows:

Analysis Found: C, 71.8; H, 9.0; N, 11.8 $C_{14}H_{20}N_2O$ requires: C, 72.4; H, 8.5; N, 12.1%;

NMR (90 MHz; CDCl$_3$) 0.89 (3H,d, J=7.2 Hz), 1.06 (3H,d, J=7.2 Hz), 1.06 (3H,t, J=7.2 Hz), 1.2 (3H,d, J=7.2 Hz), 1.5 (2H, quin, J=7.2 Hz), 2.02 (1H, sx, J=7.2 Hz), 2.5 (1H, quin, J=7.2 Hz), 3.04 (1H, s), 8.9 (2H,s), 9.1 (1H,s);

m/z 232 (M+), 189 (100%), 107.

EXAMPLE 6

2-Methyl-1-(3-methylpentyl)-1-(pyrimidin-5-yl)propan-1-ol (Compound No. 6 of Table I) was prepared by reduction of Compound No. 5 of Example 5 using the general method of Example 3. The product was a colourless oil characterised as follows:

Analysis Found: C, 70.3; H, 10.6; N, 11.2 $C_{14}H_{24}N_2O$ requires: C, 71.2; H, 10.2; N, 11.9%

Infra red 3300, 2900, 1570, 1410, 1210, 1170, 1100, 910, 870, 740, 640 cm$^{-1}$;

NMR (250 MHz; CDCl$_3$) 0.75 (9H,m) 0.92 (3H,d, J=7.2 Hz), 1.0-1.4 (6H,m), 1.6-1.9 (1H,m), 2.0 (1H, sept, J=7.2 Hz), 2.68 (1H, s), 8.73 (2H,s), 9.06 (1H,s);

m/z 237 (M+1, 100%)

EXAMPLE 7

2-Methyl-1-(4-methylpentyl)-1-(pyrimidin-5-yl)propan-1-ol (Compound No. 7 of Table I) was prepared by reduction of Compound No. 4 of Example 4 using the general method of Example 3. The product was a colourless oil characterised as follows:

Analysis Found: C, 71.4; H, 10.8; N, 11.5 $C_{14}H_{24}N_2O$ requires: C, 71.2; H, 10.2; N, 11.9%;

Infra red 3350, 2950, 1570, 1460, 1420, 1210, 910, 740, 640 cm$^{-1}$;

NMR 90 MHz; CDCl$_3$0.82 (6H,d, J=7.2 Hz), 0.95-1.5 (11H, m), 1.8-2.2 (3H,m), 2.82 (1H,s), 8.79 (2H,s), 9.08 (1H,s);

m/z 237, 236 (M+), 193, 175, 151, 107 (100%).

EXAMPLE 8

2-Methyl-1-(5-chloropen-1-yne)-1-(pyrimidin-5-yl)-propan-1-ol (Compound No. 8 of Table I) was prepared using the general method of Example 4 by reacting 5-chloropent-1-yne with 2-methyl-1-pyrimid-5-yl-propan-1-one. The product was a colourless oil characterised as follows:

Analysis Found: C, 62.4; H, 7.1; N, 10.8; Cl, 14.6 $C_{13}H_{17}ClN_2O$ requires: C, 61.8; H, 6.7; N, 11.1; Cl, 14.1%;

Infra red 3200, 2950, 2250, 1570, 1300, 1170, 1130, 1030, 960, 740, 640 cm$^{-1}$;

NMR (90 MHz; CDCl$_3$) 0.9 (3H,d, J=7.2 Hz), 1.06 (3H,d, J=7.2 Hz), 1.86-2.21 (3H,m), 2.55 (2H,t, J=7.2 Hz), 3.50 (1H,s), 3.66 (2H,t, J=7.2 Hz), 8.89 (2H,s), 9.08 (1H,s);

m/z 252 (M+), 209, 147, 107 (100%), 79.

EXAMPLE 9

2-Methyl-1-(3-methylbut-1-yne)-1-(pyrimidin-5-yl)propan-1-ol (Compound No. 9 of Table I) was prepared using the general method of Example 4 by reacting 3-methylbut-1-yne with 2-methyl-1-(pyrimid-5-yl)-propan-1-one. The product was a white solid having a melting point of 79°-79.5° C.

Analysis Found: C, 71.7; H, 8.2; N, 12.7 $C_{13}H_{18}N_2O$ requires: C, 71.6; H, 8.3; N, 12.8%;

Infra red 3200, 2950, 2230, 1570, 1410, 1320, 1240, 1210, 1050, 1030, 960, 910, 810, 740, 640 cm$^{-1}$.

NMR (250 MHz; CDCl$_3$) 0.84 (3H,d, J=7.2 Hz), 1.02 (3H,d, J=7.2 Hz), 1.23 (6H,d, J=7.2 Hz), 2.03 (1H, sept, J=7.2 Hz), 2.67 (1H, sept, J=7.2 Hz), 2.90 (1H,s), 8.94 (2H,s), 9.12 (1H,s);

m/z 219, 218 (M+), 175 (100%), 107, 41.

EXAMPLE 10

2-Methyl-1-(3,3-dimethylbut-1-yne)-1-(pyrmidin-5-yl)propan-1-ol (Compound No. 10 of Table I) was prepared using the general method of Example 4 by reacting 3,3-dimethylbut-1-yne with 2-methyl-1-(pyrimid-5-yl)-propan-1-one. The product was a white solid having a melting point of 91°-92° C.

Analysis Found: C, 72.8; H, 8.9; N, 12.2 $C_{14}H_{20}N_2O$ requires: C, 72.4; H, 8.6; N, 12.1%;

Infra red 3250, 2975, 2240, 1570, 1410, 1260, 1200, 1020, 880, 730 640 cm$^{-1}$;

NMR (250 MHz; CDCl$_3$) 0.68 (3H,d, J=7.2 Hz), 1.02 (3H,d, J=7.2 Hz); 1.23 (9H,s), 2.02 (1H, sept, J=7.2 Hz), 3.2 (1H,s), 8.89 (2H,s), 9.08 (1H,s);

m/z 233, 232 (M+), 189 (100%), 107, 43.

EXAMPLE 11

2-Methyl-1-(4-methylhex-1-yne)-1-(pyrimidin-5-yl)propan-1-ol (Compound No. 11 of Table I) was prepared using the general method of Example 4 by reacting 4-methylhex-1-yne with 2-methyl-1-(pyrimid-5-yl)-propan-1-one. The product was a yellow gum characterised as follows:

Analysis Found: C, 72.3; H, 9.1; N, 11.4 $C_{15}H_{22}N_2O$ requires: C, 73.2; H, 8.9; N, 11.4%;

Infra red 3250, 2950, 2220, 1580, 1410, 1220, 1170, 1030, 910, 730, 640 cm$^{-1}$;

NMR (250 MHz; CDCl$_3$) 0.88 (3H,d, J=7.2 Hz), 0.91 (3H,t, J=7.2 Hz), 1.02 (3H,d, J=7.2 Hz), 1.08 (3H,d, J=7.2 Hz), 1.17–1.7 (3H,m), 2.02 (1H, sept, J=7.2 Hz), 2.25 (2H,m), 4.1 (1H,s), 8.89 (2H,s), 9.09 (1H,s);

m/z 246 (M+), 203 (100%), 147, 107.

EXAMPLE 12

2-Methyl-1-(5-methylhex-1-yne)-1-(pyrimidin-5-yl)-propan-1-ol (Compound No. 12 of Table I) was prepared using the general method of Example 4 by reacting 5-methylhex-1-yne with 2-methyl-1-(pyrimid-5-yl)-propan-1-one. The product was a white solid having a melting point of 54°–55° C.

Analysis Found: C, 73.1; H, 9.5; N, 11.2 C$_{15}$H$_{22}$N$_2$O requires: C, 73.2; H, 8.9; N, 11.4%;

Infra red 3240, 2950, 2240, 1570, 1410, 1310, 1210, 1090, 1010, 910, 795, 650 cm$^{-1}$.

NMR (90 MHz; CDCl$_3$) 0.88 (3H,d, J=7.2 Hz), 0.96 (6H, d, J=7.2 Hz), 1.08 (3H,d, J=7.2 Hz), 1.34–1.8 (3H,m), 2.06 (1H, sept, J=7.2 Hz), 2.35 (2H,t, J=7.2 Hz), 2.9 (1H,s), 8.92 (2H,s), 9.10 (1H, s);

m/z 246 (M+), 203 (100%), 107.

EXAMPLE 13

2-Methyl-1-(3-methylbutyl)-1-(pyrimidin-5-yl)-propan-1-ol (Compound No. 13 of Table I) was prepared by reduction of Compound No. 9 of Example 9 using the general method of Example 3. The product was a colourless gum characterised as follows:

Analysis Found: C, 70.5; H, 11.2; N, 12.6 C$_{13}$H$_{22}$N$_2$O requires: C, 70.3; H, 9.9; N, 12.6%;

Infra red 3250, 2950, 1570, 1470, 1420, 1170, 910, 740, 640 cm$^{-1}$.

NMR (250 MHz; CDCl$_3$) 0.62 (3H,d, J=7.2 Hz), 0.7 (6H,d, J=7.2 Hz), 0.92 (3H,d, J=7.2 Hz), 1.15 (2H,m), 1.43 (1H, sept, J=7.2 Hz), 1.83 (2H,m), 1.97 (1H, sept, J=7.2 Hz), 2.9 (1H,s), 8.73 (2H,s), 9.05 (1H,s);

m/z 222 (M+), 179 (100%), 161, 151, 123, 107.

EXAMPLE 14

2,2-Dimethyl-1-(pent-1-yne)-1-(pyrimidin-5yl)propan-1ol (Compound No. 14 of Table I) was prepared using the general method of Example 4 by reacting pent-1-yne with 2,2-dimethyl-1-(pyrimid-5yl)-propan-1-one. The 2,2-dimethyl-1-(pyrimid-5-yl)-propan-1-one intermediate was prepared by reaction of 5-bromopyrimidine with 2,2-dimethylpropanaldehyde and subsequent oxidation of the product using the general methods described in Stages 1 and 2 of Example 4. Compound 14 was a yellow solid having a melting point of 64°–66° C.

Analysis Found: C, 72.7; H, 9.2; N, 12.1 C$_{14}$H$_{20}$N$_2$O requires: C, 72.4; H, 8.6; N, 12.1%;

Infra red 3200, 2950, 2750, 2210, 1560, 1400, 1210, 1140, 1100, 1050, 1030, 1000, 940, 890, 860, 760, 730 cm$^{-1}$.

NMR (90 MHz; CDCl$_3$) 1.02 (9H,s), 1.02 (3H,t, J=7.2 Hz), 1.6 (2H, sx, J=7.2 Hz); 2.3 (2H,t, J=7.2 Hz), 3.79 (1H,s), 8.94 (2H, s), 9.08 (1H,s);

m/z 232 (M+), 217, 176 (100%), 147, 107, 57, 41, 29.

EXAMPLE 15

2,2-Dimethyl-1-(pentyl)-1-(pyrimidin-5-yl)-propan-1-ol (Compound No. 15 of Table I) was prepared by reduction of Compound No. 14 of Example 14 using the general method of Example 3. The product was a white solid having a melting point of 66°–67° C.

Analysis Found: C, 71.0; H, 10.2; N, 11.7 C$_{14}$H$_{24}$N$_2$O requires: C, 71.2; H, 10.2; N, 11.9%;

Infra red 3200, 2950, 2750, 1560, 1400, 1210, 1140, 1100, 1050, 1000, 940, 890, 860, 760, 730 cm$^{-1}$.

NMR (90 MHz; CDCl$_3$) 0.9 (3H,t, J=7.2 Hz), 0.96 (9H,s), 1.12–1.42 (6H,m), 1.6–2.4 (3H,m), 8.78 (2H,s), 9.09 (1H,s);

m/z 236 (M+), 180, 165, 151, 132, 123 (100%), 107, 92, 57, 41.

EXAMPLE 16

2,2-Dimethyl-1-(4-methylpent-1-(pyrimidin-5-yl)-propan-1-ol (Compound No. 16 of Table I) was prepared using the general method of Example 14 by reacting 4-methylpent-1-yne with 2,2-dimethyl-1-(pyrimid-5-yl)-propan-1-one. The product was an off-white solid having a melting point of 65°–67° C.

Analysis Found: C, 73.5; H, 9.5; N, 11.7 C$_{15}$H$_{22}$N$_2$O requires: C, 73.2; H, 8.9; N, 11.4%;

NMR (90 MHz; CDCl$_3$); 1.01 (9H,s), 1.01 (6H,d, J=7.2 Hz), 1.86 (1H,m), 2.24 (2H,d, J=7.2 Hz), 3.36 (1H,s), 8.93 (2H,s), 9.08 (1H, s);

m/z 246 (M+), 190 (100%), 147, 57, 43, 41.

EXAMPLE 17

2,2-Dimethyl-1-(4-methylpentyl)-1-(pyrimidin-5-yl)-propan-1-ol (Compound No. 17 of Table I) was prepared by reduction of Compound No. 16 of Example 16 using the general method of Example 3. The product was a yellow gum characterised as follows:

Analysis Found: C, 72.3; H, 10.4; N, 11.0 C$_{15}$H$_{26}$N$_2$O requires: C, 72.0; H, 10.4; N, 11.2%;

Infra red 3350, 2950, 1560, 1410, 1340, 1040, 910, 900, 740, 640 cm$^{-1}$.

NMR (250 MHz; CDCl$_3$) 0.67 (6H,d, J=7.2 Hz), 0.92 (9H, s), 1.18 (4H,m), 1.47 (1H,m), 1.7–2.3 (3H,m), 8.76 (2H,s), 9.07 (1H,s);

m/z 250 (M+), 194, 123, 107, 18 (100%).

EXAMPLE 18

2,2-Dimethyl-1-(3-methylbut-1-yne)-1-(pyrimdin-5-yl)-propan-1-ol (Compound No. 18 of Table I) was prepared using the general method of Example 14 by reacting 3-methylbut-1-yne with 2,2-dimethyl-1-(pyrimid-5-yl)-propan-1-one. The product was an off-white solid having a melting point of 84°–85° C.

EXAMPLE 19

2,2-Dimethyl-1-(5-chloropent-1-yne)-1-(pyrimidin-5-yl)-propan-1-ol (Compound No. 19 of Table I) was prepared using the general method of Example 14 by reacting 5-chloropent-1-yne with 2,2-dimethyl-1-(pyrimid-5-yl)-propan-1-one. The product was a pale yellow solid having a melting point of 93°–94° C.

Analysis Found: C, 63.5; H, 7.0; N, 10.5; Cl, 13.8 C$_{14}$H$_{19}$ClN$_2$O requires: C, 63.0; h, 7.1; N, 10.5; Cl, 13.3%;

Infra red 3200, 2950, 2250, 1570, 1410, 1210, 1000, 930, 640 cm$^{-1}$.

NMR (90 MHz; CDCl$_3$) 0.98 (9H,s), 2.02 (2H, quin, J=7.2 Hz), 2.46 (2H,t, J=7.2 Hz), 3.22 (1H,s), 3.60 (2H,t, J=7.2 Hz), 8.82 (2H,s), 9.02 (1H,s);

EXAMPLES 20 AND 21

Compound Numbers 23, 24 and 60 of Table 1 were prepared using the general method of Example 4. Compound Numbers 23 and 24 were found to be oils characterised by their NMR spectra as follows:

Compound No. 23

NMR (90 MHz; CDCl$_3$)

0.85 (3H,d, J=7.2 Hz), 0.89 (3H, t, J=7.2 Hz), 1.05 (3H,d, J=7.2 Hz), 1.2-1.5 (6H,m), 2.02 (1H, sept, J=7.2 Hz), 2.29 (2H,t, J=7.2 Hz), 3.96 (1H,s), 8.88 (2H,s), 9.02 (1H,s);

Compound No. 24

NMR (90 MHz; CDCl$_3$)

0.85 (3H,d, J=7.2 Hz), 0.89 (3H, t, J=7.2 Hz), 1.07 (3H,d, J=7.2 Hz), 1.2-1.7 (8H,m), 2.06 (1H, sept, J=7.2 Hz), 2.31 (2H,t, J=−7.2 Hz), 3.95 (1H,s), 8.88 (2H,s), 9.02 (1H,s);

EXAMPLES 22 TO 27

Compound Numbers 31, 32, 33, 37, 38 and 43 in Table 1 were prepared using the general method of Example 14. The products were characterised by their melting points as indicated in Table 1.

EXAMPLES 28 TO 35

Compound Numbers 20, 21, 22, 26, 29, 30, 34 and 48 in Table 1 were prepared by the reduction of the corresponding acetylenic compounds (Compound Numbers 10, 11, 12, 23, 18, 31, 32 and 37 respectively in Table 1) using the general method of Example 3. Those products which were solids are characterised by their melting points as indicated in Table 1. The products which were gums were characterised by their NMR spectra as follows:

Compound No. 21

NMR (90 MHz; CDCl$_3$) 0.75 (6H,d, J=7.2 Hz), 0.77 (3H,t, J=7.2 Hz), 0.93 (3H,d, J=7.2 Hz), 1.0-1.35 (7H,m), 1.9 (3H,m), 2.56 (1H,s), 8.7 (2H,s), 9.03 (1H,s)

Compound No. 22

NMR (90 MHz; CDCl$_3$) 0.80 (3H, dJ=7.2Hz) 0.84 (6H,d, J=7.2Hz), 0.95 (3H,d, J=7.2Hz), 1.0-1.6 (7H,m), 1.92 (3H,m), 2.15 (1H,s), 8.7 (2H,s), 9.05 (1H,s);

Compound No. 26

NMR (90 MHz; CDCl$_3$)

0.80 (3H,d, J=7.2 Hz), 0.86 (3H,t, J=7.2 Hz), 1.0 (3H,d, J=7.2 Hz), 1.1-1.4 (10 H,m), 2.0 (3H,m), 2.4 (1H,s), 8.75 (2H,s), 9.08 (1H,s);

EXAMPLE 36

Compound Number 47 of Table 1 was prepared by the reduction of Compound Number 19 of Table 1 using the general method of Example 3, except that rhodium on charcoal was used as the catalyst in place of palladium on charcoal. The product was characterised by its melting point as in Table 1.

EXAMPLE 37

Compound No. 35 of Table 1 was prepared as follows:

To a solution of n-butyl lithium (4.8 ml of 2.5 M, 12 mmol) in dry tetrahydrofuran (40 ml) at −78° C. was added a solution of 2,2-dimethyl-1-(pyrimid-5-yl)-propan-1-one (2.0 g, 13 mmol), prepared as in Example 14. On warming to ambient temperature the reaction mixture was poured into water and extracted with ether (2×250 ml). The organic phase was collected, washed with water and brine and then dried over magnesium sulphate. The solvent was removed and the residues purified by flash chromatography. The product was a yellow oil characterised by its NMR spectrum as follows:

NMR (90 MHz; CDCl$_3$)

0.86 (3H,t, J=7.2Hz), 0.94 (9H,s), 1.1-1.4 (4H,m), 1.8-2.1 (3H,m), 8.7 (2H,s), 9.04 (1H,s);

EXAMPLE 38

Compound No. 36 of Table 1 was prepared as follows:

Stage 1

Preparation of 2,2-dimethyl-1-(4-hydroxybut-1-yne)-1-(pyrimidin-5yl)propan-1-ol.

The protected silyl ether of the desired product was prepared using the general method of Example 14 by reacting 4-(t-butyldimethysilyloxy)but-1-yne (10.0 g, 54 mmol) with 2,2-dimethyl-1-(pyrimid-5-yl)-propan-1-one (7.2 g, 54 mmol). The product was dissolved in dry tetrahhydrofuran (60 ml) and there was added molecular sieves 4 and tetrabutylammonium fluoride (27.6 ml) of lM, 0.28 mol). The reaction mixture was stirred for 24 hours, and a further quantity of tetrabutylammonium fluoride (15 ml of 1M, 15 mmol) was added and the mixture was heated to reflux for 1 hour 30 minutes. On cooling, the mixture was filtered and the solvent removed. The residues were purified by flash chromatography to give the desired product as a yellow solid (melting point 130°-131° C.).

Stage 2

The hydroxy product of stage 1 was chlorinated as follows:

To a solution of the product of stage 1 (1.3 g, 6 mmol) and triethylamine (1.01 g, 10 mmol) in dry dichloromethane was added methane sulphonyl chloride (0.86 g, 7.5 mmol) and the resulting mixture was stirred for 24 hours. The reaction mixture was then washed successively with 1M hydrochloric acid, water, aqueous sodium bicarbonate and brine, before being dried over magnesium sulphate. The solvent was removed to give a yellow oil which was dissolved in dry dimethylsulphoxide (50 ml). Anhydrous lithium chloride was added (1.6 g, 38 mmol) and the reaction heated at 70°-100° C. for 2 hours. On cooling to ambient temperature, the reaction mixture was poured into water and extracted with ether. The organic phase was collected, washed with water and brine, dried over magnesium sulphate and the solvent was removed. The resulting residues were purified by flash chromotography to give compound No. 36 as a white solid (melting point 84.5°-85° C.).

EXAMPLE 39

The procedure of Example 38 was followed to prepare compound Number 44 of Table 1 by the chlorination of 2,2-dimethyl-1-(3-hydroxypent-1-yne)-1-(pyrimidin-5-yl)propan-1-ol. The product was a yellow solid with melting point 69°-72° C.

EXAMPLE 40

Compound No. 39 in Table 1 was prepared using the general method of Example 1 by the reaction of E-2,2,6,6-tetramethylhept-4-ene-3-one (1.68 g, 10 mmol), 5-bromopyrimidine (1.59 g, 10 mmol) and n-butyl lithium. The product was a white solid having a melting point of 123°-128° C.

The ene-one intermediate of this and subsequent Examples was prepared by the following general method:

To a stirred solution of di-isoproplamine (5.16 g, 51 mmol) in dry tetrahydrofuran (50 ml) at −78° C. was added n-butyl lithium (20.4 ml of 2.5M, 51 mmol) and the reaction was stirred for 30 minutes. To this was added the appropriate methyl ketone (51 mmol) in dry tetrahydrofuran (25 ml) and the reaction was stirred for a further 30 minutes. Finally, a solution of pivaldehyde (4.39 g, 51 mmol) in dry tetrahydrofuran was added and the reaction mixture was allowed to warm to room temperature and was stirred for 16 hours. The reaction mixture was poured into water and extracted with ether before being washed, dried and purified by flash chromatography.

EXAMPLE 41

This Example illustrates the preparation of 2-methyl-1-(pent-1-ene)-1-(pyrimidin-5-yl)-propan-1-ol (Compound Number 25 of Table 1) by the reduction of Compound No. 2 of Table 1.

To a solution of 2-methyl-1-(pent-1-yne)-1-(pyrimidin-5-yl)-propan-1-ol (2.0 g 9 mmol) (prepared as in Example 2) in ethanol (180 ml) was added Lindlar catalyst (1 g). The reaction vessel was pressurised to 60 psi with hydrogen and agitated at room temperature. The course of the reaction was followed by gas-liquid chromatography and on completion (1 hour 35 minutes) the catalyst was filtered off and the solvent removed. The organic phase was collected, washed with water and brine, dried over magnesium sulphate and the solvent removed. The resultant residues were purified by flash chromatography to give a colourless gum which was characterised by NMR as follows:

NMR (90 MHz; CDCl$_3$)

0.76 (3H,t, J=7.2 Hz), 0.83 (3H, d, J=7.2 Hz), 0.98 (3H,d, J=7.2 Hz), 1.22 (2H,q, J=7.2 Hz), 2.0 (3H,m), 2.33 (1H,s) 5.68 (1H,dt, J=10.8 and 7.2 Hz), 5.98 (1H,d, J=10.8 Hz), 8.76 (2H,s), 9.04 (1H,s);

EXAMPLE 42

This Example illustrates the preparation of Compound No. 50 of Table 1, the propargyl ether of Compound No. 4 to Table 4.

Sodium hydride 0.43 g of 50% 9 mmol) was washed free of oil with petrol. The petrol was removed and dry dimethyl formamide (30 ml) was added. To this solution was added a solution of 1-(4-methylpent-1-yne)-1-(pyrimidin-5-yl)-propan-1-ol (2 g, 9 mmol) in dimethylformamide (30 ml). When the effervescence had stopped, propargyl bromide (1.07 g, 9 mmol) was added and the reaction mixture was stirred at 80° C. for 4 hours. On cooling to ambient temperature the reaction mixture was poured into water and extracted with ether. The organic phase was collected, washed with water and brine, dried over magnesium sulphate and the solvent removed. The resulting residues were purified by flash chromatography to give the product as a red oil.

NMR (90 MHz; CDCl$_3$)

0.75 (3H,d, J=7.2 Hz), 1.08 (6H,d, J=7.2 Hz), 1.15 (3H,d, J=7.2 Hz), 2.05 (2H,m), 2.32 (2H,d, J=7.2 Hz), 2.38 (1H,t, J=2.7 Hz), 3.86 (1H,dd, J=15.3 and 2.7 Hz), 4.32 (1H,dd, J=15.3 and 2.7 Hz), 8.82 (2H,s), 9.08 (1H,s);

EXAMPLES 43 TO 45

Compound Numbers 51, 52 and 53 of Table 1 were prepared in corresponding manner to that of Example 42, using respectively methyl iodide, ethyl iodide and allyl bromide. The products where characterised by NMR spectroscopy as follows:

Compound Number 51

NMR (90 MHz; CDCl$_3$)

0.7 (3H,d, J=7.2 Hz), 1.02 (6H,d, J=7.2 Hz), 1.06 (3H,d, J=7.2 Hz), 1.92 (1H sept, J=7.2 Hz), 2.04 (1H, sept, J=7.2 Hz), 2.28 (2H,d, J=7.2 Hz), 3.17 (3H,s), 8.84 (2H,s), 9.12 (1H,s);

Compound Number 52

NMR (90 MHz; CDCl$_3$)

0.75 (3H,d, J=7.2 Hz), 1.07 (6H, d, J=7.2 Hz), 1.13 (3H,d, J=7.2 Hz), 1.19 (3H,t, J=7.2 Hz), 1.99 (2H,m), 2.28 (2H,d, J=7.2 Hz), 3.04 (1H,m), 3.66 (1H,m), 8.78 (2H,s), 9.02 (1H,s);

Compound Number 53

NMR (90 MHz; CDCl$_3$)

0.75 (3H,d, J=7.2 Hz), 1.0 (6H,d, J=7.2 Hz), 1.08 (3H,d, J=7.2 Hz), 1.96 (2H,m), 2.24 (2H,d, J=7.2 Hz), 3.5 (1H,dd, J=12.6 and 5.4 Hz), 4.1 (1H, dd, J=12.6 and 5.4 Hz). 5.12 (2H,m), 5.76 (1H,m), 8.75 (2H,s), 9.02 (1H,s).

EXAMPLE 46

This Example illustrates the preparation of Compound No. 54 of Table 1, the acetate of Compound No. 4 of Table 4.

To a solution of 1-(4-methylpent-1-yne)-1-(pyrimidin-5-yl)-propan-1-ol 92 g, 9 mmol) in dry pyridine (40 ml) was added acetic anhydride (0.7 g, 9 mmol) and the reaction mixture was refluxed for 16 hours. On cooling to room temperature, the mixture was pured into water, extracted with ether, washed, dried and the solvent removed. The resulting reside was purified by flash chromatography to give a red oil, characterised by its NMR spectrum.

NMR (90 MHz; CDCl$_3$)

0.78 (3H,d, J=7.2 Hz), 1.06 (6H, d, J=7.2 Hz), 1.12 (3H,d, J=7.2 Hz), 1.98 (2H,m), 2.06 (3H,s), 2.29 (2H,d, J=7.2 Hz), 8.79 (2H,s), 9.04 (1H,s)

EXAMPLE 47

This Example illustrates the preparation of 3-fluoro-2,2-dimethyl-1-(3,3-dimethylbut-1-ene)-1-(pyrimidin-5-yl)-propan-1-ol (Compound Number 49 in Table 1).

Using the general method of Example 1, E-1-fluoro-2,2,6,6-tetramethyl-hept-4-ene-3-one (1.49 g, 8 mmol) was reacted with 5-bromopyrimidine (1.25 g, 8 mmol) and n-butyl lithium (3.15 ml of 2.5 M, 8 mmol). The product was a white solid (melting point 126°–128° C.).

EXAMPLE 48

This Example illustrates the preparation of Compound Number 55 of Table 1.

Using the general method of Example 1, E-4,4-dimethyl-1-(1'-methylcyclopropyl)pent-2-ene-1-one (1.33 g, 8 mmol) was reacted with 5-bromopyrimidine (1.25 g, 8 mmol) and n-butyl lithium (3.15 ml of 2.5M, 8 mmol). The product was a white solid (melting point 109°–110° C.).

EXAMPLE 49

This Example illustrates the preparation of Compound No 56 of Table 1.

Stage 1

Preparation of cyclopropyl-(pyrimid-5-yl)methanol.

Using the general method of Example 1, cyclopropanecarboxaldehyde (19 g, 0.27 mol) was reacted with 5-bromopyrimidine (43.2 g, 0.27 mol) and n-butyl lithium (108.6 ml of 2.5M, 0.27 mol) to give the product as a pale yellow oil.

Stage 2

Preparation of cyclopropyl pyrimid-5-yl ketone.

To a suspension of chromium (VI) oxide (42.4 g, 0.41 mol) in dry dichloromethane (1000 ml) was added dry pyridine (66 ml, 0.825 mol) and the mixture was stirred for half an hour. A solution of the product of Stage 1 (10 g, 66 mmol) in dry dichloromethane (125 ml) was then added dropwise with stirring. After 2 hours, the reaction mixture was poured into ether and filtered. The filtrate was washed with copper sulphate solution, and brine and then dried over magnesiums sulphate before removing the solvent. Flash chromatography gave the product as a pale yellow oil.

Stage 3

Using the general method of Example 4,4-methylpent-1-yne (0.82 g, 10 mmol) was reacted with the product of Stage 2 (1.48 g, 10 mmol), n-butyl lithium (4 ml of 2.5M, 10 mmol) and chlorotitanium tri-isopropoxide (10 ml of 1M, 10 mmol) to give the desired product as a colourless gum which was characterised by its NMR spectrum.

NMR (90 MHz; CDCl$_3$)
0.5–0.9 (4H,m), 0.95 (6H,d,J=7.2 Hz), 1.3–1.4 (1H,m), 1.8 (1H,m), 2.15 (2H,d,J=7.2 Hz), 4.2 (1H,br), 8.98 (2H,s), 9.12 (1H,s)

EXAMPLE 50

Compound Number 57 of Table 1 was prepared using the general method of Example 49 and was a colourless gum characterised by its NMR spectrum.

NMR (90 MHz; CDCl$_3$)
0.5–0.8 (4H,m), 0.94 (3H,t,J=7.2 Hz), 1.2–1.3 (1H,m), 1.48 (2H, sx, J=7.2 Hz), 2.18 (2H,t,J=7.2 Hz), 8.97 (2H,s), 9.12 (1H,s);

Reduction of Compound Number 57 using the general method of Example 3 gave Compound Number 58 which was characterised by its NMR spectrum as follows:

NMR (90 MHz; CDCl$_3$)
0.2–0.6 (4H,m), 0.82 (3H,t,J=7.2 Hz), 1.05–1.35 (7H,m), 1.5–2.0 (2H,m), 2.68 (1H,s), 8.85 (2H,s), 9.08 (1H,s); m/z

EXAMPLE 51

This Example illustrates the preparation of 2,2-dimethyl-1-(pent-2-yne)-1-(pyrimidin-5-yl)-propan-1-ol (Compound Number 45 of Table 1).

Stage 1

Preparation of 2,2-dimethyl-1-propargyl-1-(pyrimidin-5-yl)-propan-1-ol.

To a stirred suspension of magnesium trunings (0.58 g, 24 mmol) and mercuric chloride (catalytic) in dry ether (20 ml) at 0° C. was added a solution of proparyl bromide (2.1 g, 18 mmol) in dry ether (20 ml). After 1 hour, a solution of 2,2-dimethyl-1-primid-5-yl-propan-1-one (2.0 g, 12 mmol) in dry ether (20 ml) was added. The mixture became thick and difficult to stir. The reaction mixture was allowed to warm to ambient temperature and left for 16 hours. The reaction mixture was poured into water and extracted with ether (2×250 ml). The organics were collected, washed with water and brine, dried over magnesium sulphate and the solvent removed. The resulting residues were purified by flash chromatography to give the product as a yellow solid (0.6 g, 24.4%), melting point 174°–176° C.

Stage 2

To a solution of the product of Stage 1 (0.7 g 4 mmol) in dry tetrahydrofuran (30 ml) at −78° C. was added lithium bis(trimethylsilyl)amide (8.3 ml of 1M, 8.3 mol) and the mixture was stirred for 45 minutes. A solution of methyl sulphate (0.5 g, 0.39 mmol) in dry tetrahydrofuran (20 ml) was then added and the reaction mixture was poured into water, extracted with ether, washed with water and brine, dried and the solvent removed. The resulting residues were purified by flash chromatography to give the product as a pale yellow solid, melting point 117° C.

EXAMPLE 52

Compound Number 46 of Table 1 was prepared using the general method of Example 51, but the ethyl sulphate as alkylating agent in place of methyl sulphate. The product was a yellow solid of melting point 47°–49° C.

EXAMPLE 53

This Example illustrates the preparation of 2,2-dimethyl-1-(2-cyclopropylethyl)-1-(pyrimidin-5-yl)-propan-1-ol (Compound Number 41 of Table 1).

Stage 1

Preparation of 2,2,6,6-tetramethyl-4-(cyclopropylmethyl)-3,5-heptanedione.

To a solution of 2,2,6,6-tetramethyl-3,5-heptanedione (18.4 g) in ethanol (100 ml) was added potassium carbonate (20.7 g) followed by cyclopropylmethyl bromide (13.5 g). The mixture was heated at reflux for 16 hours. Potassium iodide (2 g) and further cyclopropylmethyl bromide (2 g) was added to the reaction mixture and reflux continued for a further 8 hours. The reaction mixture was cooled and concentrated in vacuo. To the residue was added water and the resultant mixture was extracted with ether. The ether extracts were washed with water and dried. Concentration in vacuo gave the product as an oil which was used without further purification.

Stage 2

Preparation of 2,2-dimethyl-5-cyclopropyl-pent-3-one.

The product of stage 1 (23.8 g) was added to a solution of sodium hydrxide (12.0 g) in ethanol (150 mls) and the mixture was heated at reflux for 5 hours. After being left to stand overnight, the mixture was poured into water and extracted with ether. The ether extracts were washed, dried and concentrated in vacuo and the product was distilled to give an oil which was used without further purification.

Stage 3

Using the general method of Example 1, the product of stage 2 was reacted with n-butyl lithium and 5-bromopyrimidine to give the title product as a gum which was characterised by its NMR spectrum as follow:

NMR (90 MHz; CDCl$_3$)

0.02 (2H,complex), 0.48 (2H,complex), 0.68 (1H,complex), 0.90 (1H,complex), 1.02 (9H,s), 1.22 (1H,complex), 2.08 (1H,complex), 2.32 (1H,complex), 2.40 (1H,s), 8.84 (2H,s), 9.16 (1H,s)

EXAMPLE 54

This Example illustrates the preparation of 2,2-dimethyl-1-(cyclopentylmethyl)-1-(pyrimidin-5-yl)-propan-1-ol (Compound Number 42 of Table 1).

Stage 1

Preparation of 2,2-dimethyl-4-cyclopentyl-but-3-one.

To a solution of 2-cyclopropentylacetyl chloride (11.7 g) in dry diethyl ehter (20 ml) was added under nitrogen copper (I) iodide (1.3 g). The mixture was cooled to 175° C. and t-butyl magnesium chloride (14 ml) of a 2M solution in ether) was added dropwise with stirring. After the addition was complete, the mixture was allowed to warm slowly to room temperature and was then poured into iced water containing dilute hydrochloric acid. The mixture was filtered, the ether layer separated and washed and dried. Concentration in vacuo gave the crude ketone as an oil which was used without further purification.

Stage 2

Using the general method of Example 1, the product of stage 1 was reacted with n-butyl lithium and 5-bromopyrimidine to give the title product as a colourless viscous oil which on trituration gave the title compound as a white solid of melting point 97.7°–100° C.

EXAMPLE 55

Compound Number 40 of Table 1 was prepared using the general of method of Example 54 starting with 2(cyclopent-1-enyl)acetyl chloride in stage 1. The product was a mixture of diasterioisomers in the ratio of approximately 4:3 and was a solid having a melting point of 79°–81° C.

EXAMPLE 56

Compound Number 27 of Table 1 was prepared using the general method of Example 54, except that isopropyl magnesium chloride was used in place of t-butyl magnesium chloride in stage 1. The product had a melting point of 82.2°–85.3° C.

EXAMPLE 57

Compound Number 28 of Table 1 was prepared using the general method of Example 55, except that isopropyl magnesium chloride was used in place of t-butyl magnesium chloride in stage 1. The product was a gum characterised by its NMR spectrum as follows:

NMR (90 MHz; CDCl$_3$)

0.78 (3H, 2×d, J=7 Hz), 1.0 (3H, 2×d, J=7 Hz) 0.8–2.6 (H, complex), 2.72 and 2.82 (1H,2×s), 5.25 and 5.64 (1H, 2×complex), 5.70 (1H,complex), 8.82 (2H,s), 9.12 (1H,s).

EXAMPLES 58 AND 59

Compound Numbers 61 and 63 of Table 1 were prepared by the reduction of Compound Numbers 16 and 4 respectively using the general method of Example 41. The products were characterised by their NMR spectra as follows:

Compound No 61

NMR (90 MHz; CDCl$_3$)

0.57 (3H,d,J=7.2 Hz), 0.71 (3H,d,J=7.2 Hz), 0.93 (9H,s), 1.2–2.0 (3H,m), 2.55 (1H,s), 5.75 (1H,dt,J=11.7 and 6.3 Hz), 6.3 (1H,d,J=11.7 Hz), 8.78 (2H,s), 9.06 (1H,s);

Compound No 63

NMR (90 MHz; CDCl$_3$)

0.62 (3H,d,J=7.2 Hz), 0.76 (6H,d,J=7.2 Hz), 0.94 (3H,d,J=7.2 Hz), 1.2–1.55 (1H,m), 1.7–2.1 (3H,m), 5.68 (1H,dt,J=11.7 and 6.3 Hz), 6.0 (1H,d,J=11.7 Hz), 8.79 (2H,s), 9.1 (1H,s);

TABLE II

PLANT MATERIAL USED FOR WHOLE PLANT SCREEN

| Species | Code | Variety | Growth Stage at Treatment | No. Plants per 3" Pot | Compost Type |
|---------|------|---------|---------------------------|------------------------|--------------|
| Barley | BR | Atem | 1–1.5 leaves | 4 | JIP* |
| Wheat | WW | Timmo | 1–1.5 leaves | 4 | JIP |
| Maize | MZ | Earliking | 2½ leaves | 1 | PEAT |
| Apple | AP | Red Delicious | 4–5 leaves | 1 | JIP |
| Rice | RC | Ishikari | 2–2½ leaves | 4 | JIP |

JIP* = John Innes Potting Compost.

EXAMPLE 60

Compounds 1 to 3 in Table 1 were tested for plant growth regulator activity against five species for various growth effects relevant to plant growth regulation.

Methodology

The plant species used in this screen are presented in Table II with the leaf stage at which they were sprayed. Each chemical was applied at 4000 ppm (4 kg/ha in a 1000 l/ha field volume) using a tracksprayer and a SS8004E (Teejet) nozzle.

After spray the plants were grown in a glasshouse with 25° C. day/22° C. night temperatures and supplementary lighting was supplied when necessary (from mercury vapour lamps), to provide a 16 hour photoperiod. The exception to this were the temperate cereals, wheat and barley which were grown in 16° C. day/13° C. night temperatures.

After 2–6 weeks in the glasshouse, depending on the time of year, the plants were visually assessed for morphological characteristics. Formulation blanks were used as controls to assess the plants. The results are presented in Table III.

TABLE III

| SPECIES | COMPOUND NO | R | G | A | T | I |
|---------|-------------|---|---|---|---|---|
| BR | 1 | 3 | 2 | | 1 | 3 |
| | 2 | 3 | 1 | | 3 | 3 |
| | 3 | 3 | 2 | | 3 | 3 |
| WW | 1 | 3 | 1 | | 2 | |
| | 2 | 2 | 2 | | 2 | 3 |
| | 3 | 3 | 1 | | 2 | 3 |
| RC | 1 | 2 | 2 | | 3 | 3 |
| | 2 | 3 | 2 | | 3 | 3 |
| | 3 | 3 | 2 | | 1 | 2 |

TABLE III-continued

| SPECIES | COMPOUND NO | R | G | A | T | I |
|---------|-------------|---|---|---|---|---|
| MZ | 1 | 2 | | | 2 | 2 |
| | 2 | 2 | | | | 1 |
| | 3 | | | 1 | | |
| AP | 1 | 3 | | | 1* | 3 |
| | 2 | 3 | 1 | | | 2 |
| | 3 | 3 | 1 | | | 2 |

Key:
R = Retardation
G = Greening effect
A = Apical damage
T = Tillering or side shooting
I = Interligular or internodal length reduction
All effects are scored visually on a 1-3 basis where
1 = 10-30%
2 = 31-60%
3 = 61-100%
Blank means less than 10% effect.

EXAMPLE 61

Additional compounds in Table I were tested for plant growth regulator activity using the method of Example 60 except that Tomato was included in the test as an additional species. Tomato, Ailsa Craig, was grown in a single 3 inch pot in peat and treated at the 2 to 2½ leaves growth stage. The results were presented in Table IV in which Tomato is indicated by the code TO and the Key is otherwise as for Table III.

An astrisk (*) after a score under "T" (tillering) indicated a decrease in tillering.

TABLE IVa

| Compound Number | SPECIES | | | | | | | | | |
|---|---|---|---|---|---|---|---|---|---|---|
| | BR | | | | | WW | | | | |
| | R | G | A | T | I | R | G | A | T | I |
| 5 | 3 | 1 | | 3 | 3 | 3 | 2 | | 1 | 3 |
| 6 | 2 | 1 | | | 3 | 3 | | | 1 | 3 |
| 7 | 2 | 2 | | 1 | 2 | 3 | 2 | | 3 | 3 |
| 8 | 3 | 2 | | 1 | 2 | 3 | 2 | | 3 | 3 |
| 9 | 2 | 2 | | 2 | 3 | 2 | 2 | | 2 | 3 |
| 10 | 2 | 2 | | 2 | 3 | 2 | 2 | | 1 | 3 |
| 12 | 2 | 2 | | 3 | 3 | 2 | 1 | | 1 | 2 |
| 13 | 2 | 2 | | 2 | 3 | 2 | | | 1 | 3 |
| 14 | 3 | 2 | | 3 | 3 | 3 | 2 | | 3 | 3 |
| 15 | 2 | | | | 2 | 2 | 1 | | 1 | 3 |
| 16 | 3 | 2 | | | 2 | 3 | 2 | | 3 | 3 |
| 17 | 2 | 2 | | 2 | 3 | 2 | 2 | | 2 | 3 |
| 18 | 2 | 2 | | 3 | 3 | 2 | | | 2 | 3 |
| 19 | 3 | 1 | 3 | 3 | 3 | 3 | 1 | | 3 | 3 |
| 20 | 2 | 1 | | | 2 | 3 | 2 | | | 3 |
| 21 | 2 | 1 | | 3 | 3 | 2 | 2 | | | 2 |
| 22 | 1 | | | | 1 | 2 | 2 | | 1 | 2 |
| 23 | 3 | 2 | | 1 | 3 | 2 | 2 | | | |
| 24 | 2 | | | 2* | 2 | 1 | 2 | | | |
| 25 | 3 | 3 | | 1* | 3 | 1 | 2 | | | 1 |
| 26 | | | | 2 | | 2 | 1 | | | 1 |
| 27 | | | | 2* | | 2 | 2 | | | 2 |
| 28 | 2 | | | 2* | 2 | 3 | 1 | | 3 | 3 |
| 29 | 2 | | | 2 | 2 | 2 | 2 | | 2 | 3 |
| 30 | 2 | 1 | | 2 | 3 | 3 | 2 | | 3 | 3 |
| 31 | 3 | 3 | | 1 | 3 | | 3 | 1 | 1 | 3 |
| 32 | 3 | 2 | | 1 | 3 | 2 | 1 | | | 3 |
| 33 | | | | | 2 | | 1 | | | 1 |
| 34 | | | | | 3 | | | | 1 | 1 |
| 35 | | | | | 3 | | | | 2* | |
| 36 | 3 | 3 | | 3 | 3 | 2 | 2 | | 1 | 3 |
| 37 | 3 | 3 | | 3 | 3 | 2 | 2 | | 1 | 3 |
| 38 | 3 | 3 | | 3 | 3 | 2 | 2 | | 1 | 3 |
| 39 | 3 | | | 3 | 3 | 3 | 1 | | 2 | 3 |
| 49 | | | | 3 | | 2 | 1 | | 1 | 2 |
| 55 | | | | 3 | | 2 | 1 | | 1 | 2 |
| 56 | 3 | 3 | | 3 | 3 | 2 | 2 | | 1 | 3 |

TABLE IVb

| Compound Number | SPECIES | | | | | | | | | |
|---|---|---|---|---|---|---|---|---|---|---|
| | RC | | | | | MZ | | | | |
| | R | G | A | T | I | R | G | A | T | I |
| 5 | 2 | | 1 | | 2 | — | — | — | — | — |
| 6 | 2 | | | | 2 | 2 | 1 | | | 2 |
| 7 | 2 | 1 | | | 2 | 2 | 1 | | | 2 |
| 8 | — | — | — | — | — | 3 | 1 | | 1 | 3 |
| 9 | 1 | 1 | 1 | | 1 | — | — | — | — | — |
| 10 | 2 | 1 | | | 2 | — | — | — | — | — |
| 12 | 2 | 1 | | 1 | 2 | — | — | — | — | — |
| 13 | 2 | 1 | | | 2 | — | — | — | — | — |
| 14 | 3 | 2 | | | 2 | 2 | 2 | 1 | | 3 |
| 15 | — | — | — | — | — | — | — | — | — | — |
| 16 | 3 | 2 | | 1 | 3 | 3 | 2 | | 1 | 3 |
| 17 | 2 | 1 | | 1 | 2 | — | — | — | — | — |
| 18 | 3 | 1 | | | 3 | — | — | — | — | — |
| 19 | 2 | 2 | | | 3 | — | — | — | — | — |
| 20 | 2 | 2 | | 3 | 3 | — | — | — | — | — |
| 21 | 2 | 1 | | 2 | 2 | — | — | — | — | — |
| 29 | 2 | 1 | | 1 | 3 | — | — | — | — | — |
| 30 | 2 | 2 | | 3 | 3 | — | — | — | — | — |

TABLE IVc

| Compound Number | SPECIES | | | | | | | | | |
|---|---|---|---|---|---|---|---|---|---|---|
| | AP | | | | | TO | | | | |
| | R | G | A | T | I | R | G | A | T | I |
| 5 | — | — | — | — | — | 2 | 2 | | | 2 |
| 6 | — | — | — | — | — | 2 | 2 | | | 2 |
| 7 | 3 | 1 | | | 2 | 3 | 2 | | | 3 |
| 8 | 3 | 2 | | | 3 | 3 | 2 | | | 3 |
| 9 | 3 | 1 | | | 3 | 1 | 1 | | | 1 |
| 10 | 2 | | | | 3 | | | | | |
| 12 | 2 | 1 | | | 3 | | 1 | | | |
| 13 | 3 | 2 | | | 3 | 2 | | | | 2 |
| 14 | 3 | 3 | | 1 | 3 | 3 | 2 | | | 2 |
| 15 | — | — | — | — | — | 2 | 2 | | | 2 |
| 16 | 3 | 3 | | | 3 | 3 | 2 | | | 3 |
| 17 | 3 | 1 | | | 3 | 1 | 1 | | | 1 |
| 18 | 3 | 2 | | | 3 | 3 | | | | 3 |
| 19 | 3 | 1 | | | 3 | 2 | 2 | | | 2 |
| 20 | 3 | 2 | | | 3 | 3 | 2 | | | 3 |
| 21 | 2 | | | | 2 | 2 | 2 | | | 2 |
| 22 | 1 | | | | 1 | 2 | 2 | 1 | | 2 |
| 23 | — | — | — | — | — | 2 | 2 | | | 2 |
| 24 | — | — | — | — | — | 1 | 2 | | | |
| 25 | — | — | — | — | — | 1 | 2 | | | 1 |
| 26 | — | — | — | — | — | 2 | 1 | | | 1 |
| 27 | — | — | — | — | — | 2 | 2 | | | 2 |
| 28 | — | — | — | — | — | 3 | 1 | | | 3 |
| 29 | 2 | 1 | | | 2 | 2 | 1 | | | 2 |
| 30 | 2 | | | | 2 | 2 | 2 | | | 2 |
| 31 | — | — | — | — | — | 3 | 2 | | | 3 |
| 32 | — | — | — | — | — | 2 | 2 | | | 1 |
| 33 | — | — | — | — | — | 2 | 1 | | | 1 |
| 34 | — | — | — | — | — | 2 | | | | 1 |
| 35 | — | — | — | — | — | 2 | | | | 2 |
| 36 | — | — | — | — | — | 2 | 2 | | | 2 |
| 37 | — | — | — | — | — | | | | | |
| 38 | — | — | — | — | — | 3 | 2 | | | 3 |
| 39 | — | — | — | — | — | 3 | 2 | | | 3 |
| 49 | — | — | — | — | — | 2 | 1 | | | 1 |
| 55 | — | — | — | — | — | 2 | 2 | | | 2 |
| 56 | — | — | — | — | — | 1 | 1 | | | 1 |

EXAMPLE 62

Intermediate Retardant Test

Methodology

Three species are involved in this test RICE, SPRING-BARLEY and APPLES. The variety and growth stages at spray are outlined in Table V. Compounds were applied at 500 ppm and 2000 ppm respectively (0.5 kg and 2 kg/ha$^{-1}$ at a field volume of 1000 l/ha$^{-1}$) as an overall spray except in the case of certain tests on APPLES. This gives a foliar and root component in the test, i.e., this test will detect the activity of both root and foliar acting compounds. The intermediate retardant test on APPLES of which the results are given in Table IX was different, in that a foliar (only) spray at 2000 ppm was compared with a root drench, also at 2000 ppm. The rice was grown in 4" 'paddy' pots, i.e., the roots and bottom of the stems are immersed in water under conditions corresponding to those in paddy fields. Spring barley and apples were grown in 4" pots. The plants were assessed for height to top-most ligule at approximately 28 days after treatment for spring barley and rice and for height to apex at approximately 28 days after the treatment for apples. The results are presented in Tables VI to IX. In each case the result for the 500 ppm and 2000 ppm test for each compound is compared to the height of the formulation blank in that test, presented as a percentage reduction in height compared to the formulation blank. A blank indicates that the compound was substantially inactive as a retardant at that particular rate of application.

TABLE V

PLANT MATERIAL FOR INTERMEDIATE RETARDANT TEST

| Species | Variety | Growth Stage at Treatment | No Plants per 4" Pot | Compost Type |
|---|---|---|---|---|
| Spring Barley | Atem/-kym | 3 leaves | 4 | JIP 1 |
| Rice | Ishikari | 3–4 leaves | 2 | SM2:JIP 1 |
| Apples | Red Delicious | 5–10 cm high | 1 | SM2:JIP 1 |

JIP 1 = John Innes Potting Compost.
SM2 = a mixture of loam and grit.

TABLE VI

Percentage Reduction in Height of Rice.
(Compared to formulation blank).

| COMPOUND NO | Rate | |
|---|---|---|
| | 500 ppm | 2000 ppm |
| 1 | 6.06 | 23.0 |
| 2 | 18.0 | 46.0 |
| 3 | 17.0 | 47.0 |
| 5 | 39 | 68 |
| 6 | 26 | 50 |
| 7 | 31 | 45 |
| 8 | 43 | 54 |
| 9 | 11 | 18 |
| 10 | 9 | 20 |
| 11 | 4 | 14 |
| 12 | 5 | 8 |
| 13 | 8 | 9 |
| 14 | 63 | 76 |
| 15 | 13 | 39 |
| 16 | 59 | 65 |
| 17 | 7 | 10 |
| 18 | 13 | 15 |
| 19 | 11 | 39 |

TABLE VII

Percentage Reduction in Height of Spring Barley.
(Compared to formulation blank).

| COMPOUND NO | Rate | |
|---|---|---|
| | 500 ppm | 2000 ppm |
| 1 | 1.3 | 12.1 |
| 2 | 1.0 | 20.0 |
| 3 | | 11.0 |
| 5 | 38 | 72 |
| 6 | 22 | 57 |
| 7 | 23 | 47 |
| 8 | 31 | 63 |
| 9 | 20 | 49 |
| 10 | 29 | 62 |
| 11 | 5 | 47 |
| 12 | 3 | 19 |
| 13 | 2 | 11 |
| 14 | 51 | 68 |
| 15 | 14 | 33 |
| 16 | 66 | 88 |
| 17 | 2 | 28 |
| 18 | 17 | 55 |
| 19 | 31 | 57 |

TABLE VIII

Percentage Reduction in Height of Apples.
(Compared to formulation blank).

| COMPOUND NO | Rate | |
|---|---|---|
| | 500 ppm | 2000 ppm |
| 1 | 10.8 | 39.2 |
| 2 | 10.5 | 52.1 |
| 3 | | 34.1 |

TABLE IX

Percentage Reduction in Height of Apples.
(Compared to formulation blank).

| COMPOUND NO | Rate | |
|---|---|---|
| | 2000 ppm (Foliar) | 2000 pmm (Root) |
| 5 | 25.6 | 76.1 |
| 6 | 18.8 | 72.1 |
| 7 | 12.0 | 45.0 |
| 8 | 6.0 | 49.3 |
| 9 | 0 | 63 |
| 10 | 4 | 69 |
| 11 | 6 | 55 |
| 12 | 2 | 58 |
| 13 | 7 | 70 |
| 14 | 23.0 | 58.5 |
| 15 | 44.2 | 71.1 |
| 16 | 6.0 | 47.0 |
| 17 | 17 | 66 |
| 18 | 0 | 69 |
| 19 | 54 | 65 |

EXAMPLE 63

In this Example, compounds of the present invention were compared with the closest prior art compound disclosed in British patent specification No. 1,218,623 and described therein on page 6, line 45 as alpha, alpha-bis(isopropyl)-5-pyrimidinemethanol (or in the nomenclature used herein, 2-methyl-1-isopropyl-1-(pyrimidin-5-yl)-propan-1-ol). The prior art compound was prepared using the general method of Example 1 by reacting 5-bromopyrimidine with di-isopropyl ketone in the presence of n-butyl lithium.

The prior art compound was compared with compounds of the present invention in side-by-side comparisons using the Intermediate Retardant Test described in Example 62, and the results are given in Tables X to XII where 'A' is the prior art compound, 2-methyl-1-isopropyl-1-(pyrimidin-5-yl)-propan-1-ol).

TABLE X

Percentage Reduction in Height of Rice.
(Compared to formulation blank).

| COMPOUND NO | Rate | |
|---|---|---|
| | 500 ppm | 2000 ppm |
| A | 2 | 0 |
| 2 | 27 | 69 |
| 3 | 17 | — |
| 4 | 45 | 66 |

TABLE XI

Percentage Reduction in Height of Spring Barley.
(Compared to formulation blank).

| COMPOUND NO | Rate | |
|---|---|---|
| | 500 ppm | 2000 ppm |
| A | 0 | 0 |
| 2 | 25 | 59 |
| 3 | 0 | — |
| 4 | 53 | 64 |

TABLE XII

Percentage Reduction in Height of Apples.
(Compared to formulation blank).

| COMPOUND NO | Rate | |
|---|---|---|
| | 2000 ppm (Foliar) | 2000 ppm (Root) |
| A | 0 | 23.5 |
| 2 | 41.8 | 64.4 |
| 3 | 14.2 | 62.7 |
| 4 | 46.8 | 64.6 |

TABLE XIII

PLANT MATERIAL USED FOR WHOLE PLANT SCREEN

| Species | Code | Variety | Growth Stage at Treatment | No Plants per 3" Pot | Compost Type |
|---|---|---|---|---|---|
| Barley | BR | Atem | 2-3 leaves | 3 | JIP* |
| Apple | AP | Red Delicious | 4-5 leaves | 1 | JIP |
| Rice | RC | Ishikari | 3-4 leaves | 2 | JIP |
| Sunflower | SR | | 2-3 leaves | 1 | JIP |

JIP* = John Innes Potting Compost.

EXAMPLE 64

The general Intermediate Retardant Test described in Example 62 was modified by the addition of Sunflowers (SR) and the variety and growth stages at spray are outlined in Table XIII. Apart from the changes indicated, growing conditions for barley, rice and apples were as in Example 62 and growing conditions for Sunflower were as for apples. Test compounds were applied to barley, rice and apples as whole plant (overall) sprays at a rate of 2000 g/ha. Test compounds were applied to sunflowers separately as a foliar only spray at a rate of 2000 g/ha and as a root drench at a rate of 2000 g/ha.

Barley and rice were assessed for height to topmost ligule 21 days after treatment; apples were assessed for height to apex at 21 days after treatment; and sunflowers were assessed for height to apex at 14 days after treatment. The results are expressed as percentage reduction in height compared with the formulation blank in Table XIV.

TABLE XIV

| Compound Number | PERCENTAGE REDUCTION IN HEIGHT | | | | |
|---|---|---|---|---|---|
| | BR | RC | AP | SR (Root) | SR (Foliar) |
| 23 | 29 | 54 | 50 | 45 | 2 |
| 24 | 6 | 17 | 37 | 3 | 0 |
| 25 | 52 | 55 | 31 | 54 | 0 |
| 31 | 69 | 77 | 50 | 51 | 19 |
| 32 | 17 | 46 | 30 | 37 | 13 |

EXAMPLE 65

This Example illustrates the fungicidal properties of compounds 1,7,16,19 and 55 when tested against a variety of foliar fungal diseases of plants. The technique employed was as follows.

The plants were grown in John Innes Possitng Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i/dry soil. Tween 20, to give a final concentration of 0.05%, was added when the sprays were applied to cereals.

For most of the tests the compounds were applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

4 = no disease
3 = trace - 5% of disease on untreated plants
2 = 6-25% of disease on untreated plants
1 = 26-59% of disease on untreated plants
0 = 60-100% of disease on untreated plants The results are shown in Table XV.

TABLE XV

| COMPOUND NUMBER | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PUCCINIA RECONDITA (WHEAT) | PHYTOPHTHORA INFESTANS (TOMATO) |
|---|---|---|---|---|---|---|---|
| 1 | 4 | — | 0 | 0 | 0 | 0 | 0 |
| 7 | 4 | — | 0 | 0 | — | 0 | 0 |
| 16 | 4 | 4 | 3 | 4 | 0 | 3 | 0 |
| 19 | 4 | — | 0 | 4 | 0 | 4 | 0 |

TABLE XV-continued

| COMPOUND NUMBER | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) | PLASMOPARA VITICOLA (VINE) | PUCCINIA RECONDITA (WHEAT) | PHYTO-PHTHORA INFESTANS (TOMATO) |
|---|---|---|---|---|---|---|---|
| 55 | 4 | — | 0 | 4 | 0 | 4 | 0 |

The manner in which the compounds of the present invention may be formulated into compositions suitable for application is shown generally in the following indicative illustrations numbered as Examples 66 to 75.

EXAMPLE 66

An emulsifiable concentrate is made up by mixing the following ingredients, and stirring the mixture until all the constituents were dissolved.

| | |
|---|---|
| Compound of Table I | 10% |
| Calcium dodecylbenzensulphate | 5% |
| "SYNPERONIC" NP13 | 5% |
| "Aromasol" H | 80% |

EXAMPLE 67

A composition in the form of grains readily dispersible in a liquid, e.g. water, is prepared by grinding together the first three ingredients in the presence of added water and then mixing in the sodium acetate. The resultant mixture is dried and passed through a British Standard mesh sieve, size 44–100, to obtain the desired size of grains.

| | |
|---|---|
| Compound of Table I | 50% |
| "Dispersol" T | 25% |
| "SYNPERONIC" NP5 | 1.5% |
| Sodium acetate | 23.5% |

EXAMPLE 64

The following ingredients are ground together to produce a powder formulation readily dispersible in liquids.

| | |
|---|---|
| Compound of Table I | 45% |
| "Dispersol" T | 5% |
| "SYNPERONIC" NX | 0.5% |
| "Cellofas" B600 | 2% |
| China clay GTY powder | 47.5% |

EXAMPLE 69

The active ingredient is dissolved in acetone and the resultant liquid is sprayed on to the granules of attapulgite clay. The solvent is then allowed to evaporate to produce a granular composition.

| | |
|---|---|
| Compound of Table I | 5% |
| Attapulgite granules | 95% |

EXAMPLE 70

A composition suitable for use as a seed dressing is prepared by mixing the three ingredients.

| | |
|---|---|
| Compound of Table I | 50% |
| Mineral oil | 2% |
| China clay | 48% |

EXAMPLE 71

A dusting powder is prepared by mixing the active ingredient with talc.

| | |
|---|---|
| Compound of Table I | 5% |
| Talc | 95% |

EXAMPLE 72

A flowable formulation is prepared by bead-milling the constituents set out below and then forming an aqueous suspension of the ground mixture with water.

| | |
|---|---|
| Compound of Table I | 40% |
| "Dispersol" T | 4% |
| "SYNPERONIC" NP5 | 1% |
| Water | 55% |

EXAMPLE 73

A dispersible powder formulation is made by mixing together the ingredients set out below and then grinding the mixture until all were thoroughly mixed.

| | |
|---|---|
| Compound of Table I | 25% |
| "Aerosol" OT/B | 2% |
| "Dispersol" A.C. | 5% |
| China clay | 28% |
| Silica | 40% |

EXAMPLE 74

This Example illustrates the preparation of a dispersible powder formulation. The ingredients are mixed and the mixture then ground in a comminution mill.

| | |
|---|---|
| Compound of Table I | 25% |
| "PERMINAL" BX | 1% |
| "Dispersol" T | 5% |
| Polyvinylpyrrolidone | 10% |
| Silica | 25% |
| China clay | 34% |

EXAMPLE 75

The ingredients set out below are formulated into dispersible powder by mixing then grinding the ingredients.

| | |
|---|---|
| Compound of Table I | 25% |
| "Aerosol" OT/B | 2% |
| "Dispersol" A | 5% |

| | |
|---|---|
| -continued | |
| China clay | 68% |

In Examples 66 to 75 the proportions of the ingredients given are by weight.

There now follows an explanation of the compositions or substances represented by the various Trade Marks and Trade Names mentioned above.

| | |
|---|---|
| "SYNPERONIC" NP13 | a condensate of nonyl phenol (1 mole) with ethylene oxide (13 moles). |
| "AROMASOL" H | a solvent mixture of alkylbenzenes. |
| "DISPERSOL" T AND AC | a mixture of sodium sulphate and a condensate of formaldehyde with sodium naphthalene sulphonate. |
| "SYNPERONIC" NP5 | a condensate of nonyl phenol (1 mole) with naphthalene oxide (5.5 moles). |
| CELLOFAS B600 | a sodium carboxymethyl cellulose thickener. |

We claim:

1. A pyrimidine derivative having the formula (I):

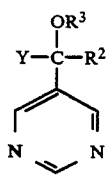

and stereoisomers thereof, wherein Y is cyclopropyl optionally substituted by lower alkyl or halogen or 1-methylcyclopropyl optionally substituted by lower alkyl or halogen or Y is the group:

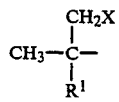

wherein $R^1$ is hydrogen or methyl; X is hydrogen or halogen; $R^2$ is an alkyl, cycloalkyl, cycloalkylalkyl or alkylcycloalkyl group, each of said groups having a total of from 4 to 8 carbon atoms, said alkyl group being optionally substituted by halogen, and said cycloalkyl, cycloalkylalkyl or alkylcycloalkyl groups being optionally substituted by halogen or, in the cycloalkyl ring, by lower alkyl; or $R^2$ is an alkenyl, cycloalkenyl, cycloalkenylalkyl, or alkylcycloalkenyl group, each of said groups having a total of from 4 to 8 carbon atoms, said alkenyl group being optionally substituted by halogen, and said cycloalkenyl, cycloalkenylalkyl or alkylcycloalkenyl groups being optionally substituted by halogen or, in the cycloalkenyl ring, by lower alkyl; or $R^2$ is an alkynyl group having a total of from 4 to 8 carbon atoms optionally substituted by halogen; and $R^3$ is hydrogen, an alkyl group having from 1 to 4 carbon atoms, an alkenyl group having from 3 to 4 carbon atoms or an alkynyl group having from 3 to 4 carbon atoms; and agrochemically acceptable salts and esters.

2. A pyrimidine derivative according to claim 1 wherein $R^2$ is an alkenyl group of formula:

wherein $R^4$ is an alkyl group having from (2-m) to (6-m) carbon atoms optionally substituted by halogen or a cycloalkyl or cycloalkylalkyl group having from 3 to (6-m) carbon atoms optionally substituted by halogen or, in the cycloalkyl ring by lower alkyl, and m is an integer from 0 to 2.

3. A pyrimidine derivative according to claim 2 wherein $R^2$ is an alkenyl group of formula:

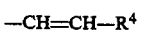

wherein $R^4$ is an alkyl group having from 2 to 6 carbon atoms optionally substituted by halogen.

4. A pyrimidine derivative according to claim 1 wherein $R^2$ is an alkynyl group of formula:

wherein $R^5$ is an alkyl group having from (2-n) to (6-n) carbon atoms optionally substituted by halogen or a cycloalkyl or cycloalkylalkyl group having from 3 to (6-n) carbon optionally substituted by halogen or, in the cycloalkyl ring, by lower alkyl, and n is an integer from 0 to 2.

5. A pyrimidine derivative according to claim 4 wherein $R^2$ is an alkynyl group of formula:

wherein $R^5$ is an alkyl group having from 2 to 6 carbon atoms optionally substituted by halogen.

6. A pyrimidine derivative according to claim 5 wherein $R^4$ is an alkyl group having from 3 to 4 carbon atoms optionally substituted by halogen.

7. A pyrimidine derivative according to claim 1 wherein the optional substituent which may be present in the group $R^2$ is chlorine or fluorine.

8. A pyrimidine derivative according to claim 1 wherein, in the group Y in formula (I), the group X is chlorine or fluorine or the optional substituent which may be present in the cyclopropyl or 1-methylcyclopropyl group is chlorine or fluorine.

9. A pyrimidine derivative according to claim 1 wherein $R^3$ is hydrogen, methyl, ethyl, allyl or propargyl.

10. A plant growth regulating composition comprising a plant growth regulating amount of a pyrimidine derivative according to claim 1 and an agrochemically acceptable carrier or diluent.

11. A fungicidal composition comprising a fungicidal amount of a pyrimidine derivative according to claim 1 and an agrochemically acceptable carrier or diluent.

* * * * *